US007736421B2

(12) United States Patent
Hering et al.

(10) Patent No.: US 7,736,421 B2
(45) Date of Patent: Jun. 15, 2010

(54) HIGH SATURATION RATIO WATER CONDENSATION DEVICE AND METHOD

(75) Inventors: Susanne Hering, Berkeley, CA (US); Gregory Lewis, Berkeley, CA (US)

(73) Assignee: Aerosol Dynamics Inc., Berkeley, CA (US)

(*) Notice: Subject to any disclaimer, the term of this patent is extended or adjusted under 35 U.S.C. 154(b) by 0 days.

(21) Appl. No.: 11/868,163

(22) Filed: Oct. 5, 2007

(65) Prior Publication Data

US 2008/0083274 A1 Apr. 10, 2008

Related U.S. Application Data

(60) Provisional application No. 60/850,553, filed on Oct. 10, 2006.

(51) Int. Cl.
*B01D 47/06* (2006.01)

(52) U.S. Cl. ........................................................ 95/225

(58) Field of Classification Search .................... 95/225
See application file for complete search history.

(56) References Cited

U.S. PATENT DOCUMENTS

| | | | |
|---|---|---|---|
| 2,684,008 | A | 7/1954 | Vonnegut |
| 3,694,085 | A | 9/1972 | Rich |
| 3,806,248 | A | 4/1974 | Sinclair |
| 4,449,816 | A | 5/1984 | Kohsaka et al. |
| 4,790,650 | A | 12/1988 | Keady |
| 4,950,073 | A | 8/1990 | Sommer |
| 5,026,155 | A | 6/1991 | Ockovic et al. |
| 5,118,959 | A | 6/1992 | Caldow et al. |
| 5,239,356 | A | 8/1993 | Hollander et al. |
| 5,519,490 | A | 5/1996 | Nakata et al. |
| 5,659,388 | A | 8/1997 | Scheer et al. |
| 5,675,405 | A | 10/1997 | Schildmeyer et al. |
| 5,699,679 | A | 12/1997 | Wu et al. |
| 5,872,622 | A | 2/1999 | Schildmeyer et al. |
| 5,903,338 | A | 5/1999 | Mavlev et al. |
| 6,230,572 | B1 | 5/2001 | Pui et al. |
| 6,330,060 | B1 | 12/2001 | Flagan et al. |
| 6,379,419 | B1 | 4/2002 | Celik et al. |
| 6,506,345 | B1 | 1/2003 | Lee et al. |

(Continued)

FOREIGN PATENT DOCUMENTS

WO WO03065005 A2 * 8/2003

OTHER PUBLICATIONS

International Appln. No. PCT/US07/80728, filed Oct. 8, 2007, PCT International Search Report and Written Opinion dated Mar. 6, 2008.

(Continued)

*Primary Examiner*—Walter D Griffin
*Assistant Examiner*—Bobby Ramdhanie
(74) *Attorney, Agent, or Firm*—Vierra Magen Marcus & DeNiro LLP

(57) ABSTRACT

An apparatus and method for producing a region of vapor super-saturation and particle growth in a laminar flow by surrounding the particle flow with a saturated or super-saturated sheath flow from which vapor diffuses into the aerosol flow. This method is applicable when the mass diffusivity of the condensing vapor is greater than the thermal diffusivity of the carrier gas, such as is the case when water vapor diffuses into air.

17 Claims, 6 Drawing Sheets

U.S. PATENT DOCUMENTS

| | | |
|---|---|---|
| 6,712,881 B2 | 3/2004 | Hering et al. |
| 2002/0134137 A1 | 9/2002 | Ondov et al. |
| 2003/0020050 A1 | 1/2003 | Heintzenberg et al. |

OTHER PUBLICATIONS

Aitken, "On the Number of Dust Particles in the Atmosphere", Transaction of the Royal Society of Edinburgh, vol. XXXV, 1888.

Bricard, et al., "Detection of Ultra-Fine Particles by Means Of A Continuous Flux Condensation Nuclei Counter", Proceedings of a symposium by U.S. Environmental Protection Agency held in Minneapolis, Minnesota, May 28-30, 1975.

Kousaka, et al., "Development of a Mixing Type Condensation Nucleus Counter", J. Aerosol Sci., vol. 13, No. 3, pp. 231-240, 1982.

Chuang, et al., "A theoretical analysis of cloud condensation nucleus (CCN) instruments", Journal of Geophysical Research, vol. 106, No. D4, pp. 3449-3474, Feb. 27, 2001.

Wang, et al., "Fast Mixing Condensation Nucleus Counter: Application to Rapid Scanning, Differential Mobility Analyzer Measurements", Aerosol Sci. & Techn. 36: 678-689, 2002.

Demokritou, et al., "A HIgh Volume Apparatus for the Condensational Growth of Ultrafine, Particles for Inhalation Toxicological Studies", Aerosol Sci & Techn. 36: 1061-1072, 2002.

Stolzenburg, et al., "An Ultrafine Aerosol Condensation Nucleus Counter", Aerosol Science and Technology 14: 48-65, 1991.

Hoppel, et al., "A Segmented Thermal Diffusion Chamber for Continuous Measurements, of CN", J. Aerosol Sci., vol. 10, pp. 369-373, 1979.

International Appln. No. PCT/US07/80728, filed Oct. 8, 2007, International Preliminary Report on Patentability and Written Opinion of the International Searching Authority dated Apr. 15, 2009.

\* cited by examiner

HIGH SATURATION RATIO WATER CONDENSATION DEVICE AND METHOD

PRIORITY DATA

The present application claims priority to U.S. Provisional Patent Application No. 60/850,553, filed Oct. 10, 2006 entitled "High Saturation Ratio Water Condensation Device And Method," having inventors Susanne Hering and Gregory Lewis.

TECHNICAL FIELD

This technology relates to the detection and measurement of airborne particles and aerosols through condensational growth, with subsequent detection or collection.

DESCRIPTION OF RELATED ART

For many decades, condensational growth has been used to enable the detection and measurement of small airborne particles, most of which have diameters smaller than the wavelength of visible light. The concept was first introduced in the nineteenth century and continues to be used today. Condensation is used to grow particles to a size that can be detected optically, thereby providing a means to readily measure airborne particle number concentrations. Condensational enlargement is also used to enable the aerodynamic focusing or collection of particles for chemical or exposure analyses.

Condensational growth of ultrafine particles may conventionally be done by one of three techniques: (1) adiabatic expansion, (2) turbulent mixing, or (3) cold-walled condenser tubes. Each of these methods creates a region of super-saturation, wherein the concentration of the condensing vapor is greater than its equilibrium vapor pressure at the local gas temperature. Adiabatic expansion produces a high super-saturation of water vapor, allowing the activation of very small particles, but is inherently a semi-continuous flow process. Turbulent mixing is the process of mixing two saturated streams at differing temperatures, which produces super-saturation because of the non-linear nature of the vapor condensation curve. Turbulent mixing is compatible with a continuous flow, and is effective for a variety of condensing vapors, including water, but does not produce a well-defined super-saturation profiles. Cold-walled condensers pass the sample air flow through a saturator followed by through a cold-walled condenser. These require that the condensing vapor be a slowly diffusing substance, such as butanol. This approach cannot be used with water because water diffuses more quickly than does air such that it is depleted from the centerline before the flow cools.

For many applications it is desirable to have a continuous flow system, with well defined super-saturation profiles, such as afforded by the butanol-based condensation counters, but with water as the condensing fluid. Water is nontoxic and inexpensive. Water is preferred over butanol or other fluids when collecting particles for chemical analysis. Water-based condensation counters are suitable for measurements in offices, homes and other inhabited locations. They present less of a problem for operation in clean rooms, such as those used for microchip manufacture.

U.S. Pat. No. 6,712,881 introduced a water condensation method that combines the advantages of the continuous flow instruments with the advantages of water condensation. With this method aerosol, or aerosol plus particle-free sheath air, flows in a laminar manner through a device whose walls are wetted and held at a temperature warmer than the entering flow. Because the mass diffusivity of water vapor (~0.265 cm$^2$/s) is larger than the thermal diffusivity of air (~0.215 cm$^2$/s), the transport of water vapor from the warm, wetted walls is faster than the rate at which the flow warms. The result is the creation of a region of water vapor super-saturation which has a maximum along the centerline of the flow, where super-saturation is defined as a water vapor content in excess of the equilibrium water vapor content.

Commercial implementations of laminar-flow, water-based condensational particle counters based on this method provides detection of particles as small as 5 nm in diameter. This instrument uses a tube lined with a wetted wick through which the aerosol sample stream passes. The walls of the first portion of this wick-lined tube are held at a temperature $T_c$, and act as a "preconditioner". The walls of the second portion of the tube are heated to at temperature $T_h$ greater than $T_c$. In this second portion, called the "growth region", the relatively faster diffusion of water vapor from the warm, wet walls as compared to the warming of the flow creates a region of supersaturation, particle activation and condensational growth.

A second commercial version of this water-based condensation particle counter uses a particle-free sheath air which surrounds the particle-laden flow so as to confine the particles to the centerline, where the highest super-saturation is achieved. As with the first version, there is a single, wet-walled tube through which the entirety of the flow, both sheath and aerosol, passes. All of the air flow that enters the second, condensational growth region is at an approximately uniform temperature and water vapor saturation. There is no difference in the temperature and saturation conditions of the aerosol and sheath portions of the flow. By operating with a cooler preconditioner region, and a warmer growth region, this instrument is able to activate, grow and detect particles as small as 3 nm.

Experience with these instruments has shown that the extent of vapor super-saturation achieved in these systems is not as high as predicted for flow through a wet-walled tube with a sharp, step-function increase in wall temperature. Analysis of the diffusion of water vapor from the wetted walls and of the thermal transport into the flow in the growth region yields a higher vapor super-saturation, and smaller particle activation size, than is measured experimentally. In practice, there is a temperature gradient along the walls of the tube that arises from the evaporative and convective cooling at the walls. Instead of a sharp transition from colder to warmer temperature at the entrance of the growth region, there is a gradient along the direction of the flow, and a corresponding decrease in the extent of super-saturation achieved.

SUMMARY

In one embodiment, the technology is a method comprising the steps of: providing a growth chamber having walls at a first temperature [Tw]; providing a sheath flow at a second temperature [Ts] containing a high concentration of a condensable vapor; introducing a particle laden flow in a laminar manner with the sheath flow, the particle laden flow being introduced at a third temperature [Ta] lower than the first temperature and the second temperature. Within the chamber containing the combined flows a region of vapor super-saturation is created as a result of the differential rates of thermal and mass transport. As a result, the vapor condenses on the particles, enlarging them into droplets for subsequent detection, collection or manipulation.

In a second embodiment, the technology is a particle condensation apparatus. The apparatus includes a growth chamber having wetted walls maintained at a first temperature. A sheath conditioner having an inlet receiving a sheath flow is provided. The flow includes a condensable vapor. The sheath conditioner has an outlet outputting the sheath flow at a second temperature and at a partial pressure near a saturation value of the sheath flow into the growth chamber. An aerosol conditioner is provided. The aerosol conditioner has an inlet receiving a particle laden and an outlet outputting the flow in the growth chamber at a third temperature. The outlet is positioned to combine the particle laden flow with the sheath flow in a laminar manner. The second temperature is greater than the third temperature.

BRIEF DESCRIPTION OF THE DRAWINGS

FIGS. 6 and 7 show the saturation profiles for a the present technology wherein the sheath flow is at 200% RH.

FIG. 9 depicts the supersaturation profiles possible with the configuration of FIG. 8.

DETAILED DESCRIPTION

The present technology creates vapor super-saturation of a highly diffusive species in a laminar flow of a carrier gas. In one embodiment, the creation of a region of water vapor super-saturation in a flow of air is disclosed, but the technology is more generally applicable to any case where the mass diffusion coefficient of the diffusing vapor is higher than the thermal diffusivity of the carrier gas. This technology comprises an apparatus and method for enlarging particle size through condensational growth in a laminar, thermally diffusive flow.

The present technology uses a warm sheath flow containing a condensable vapor at a concentration near, or even greater than, its saturation value. This sheath flow is introduced in a laminar manner to surround a colder particle laden flow. The condensable vapor from the sheath flow diffuses into the colder particle laden flow, while at the same time the flow warms from the presence of the surrounding warm air. When the mass diffusivity of the vapor is greater than the thermal diffusivity of the carrier gas, the vapor reaches the center, colder flow before more quickly than it is warmed. This creates a region of vapor super-saturation that activates condensational growth on pre-existing particles. Because the transport of vapor from the sheath flow into the particle flow is by diffusion only, we refer to the method of the present technology as "diffusive mixing".

The sheath flow in the present technology is not at the same temperature and relative humidity conditions as the particle-laden flow. Instead, the present technology uses a vapor-laden sheath flow that is warmer than the particle-laden flow. This diffusive mixing method provides an immediate, high water vapor content in the air stream surrounding the aerosol flow, and overcomes the convective and evaporative cooling that is observed to adversely affect the system performance with the prior design.

Figure 1:
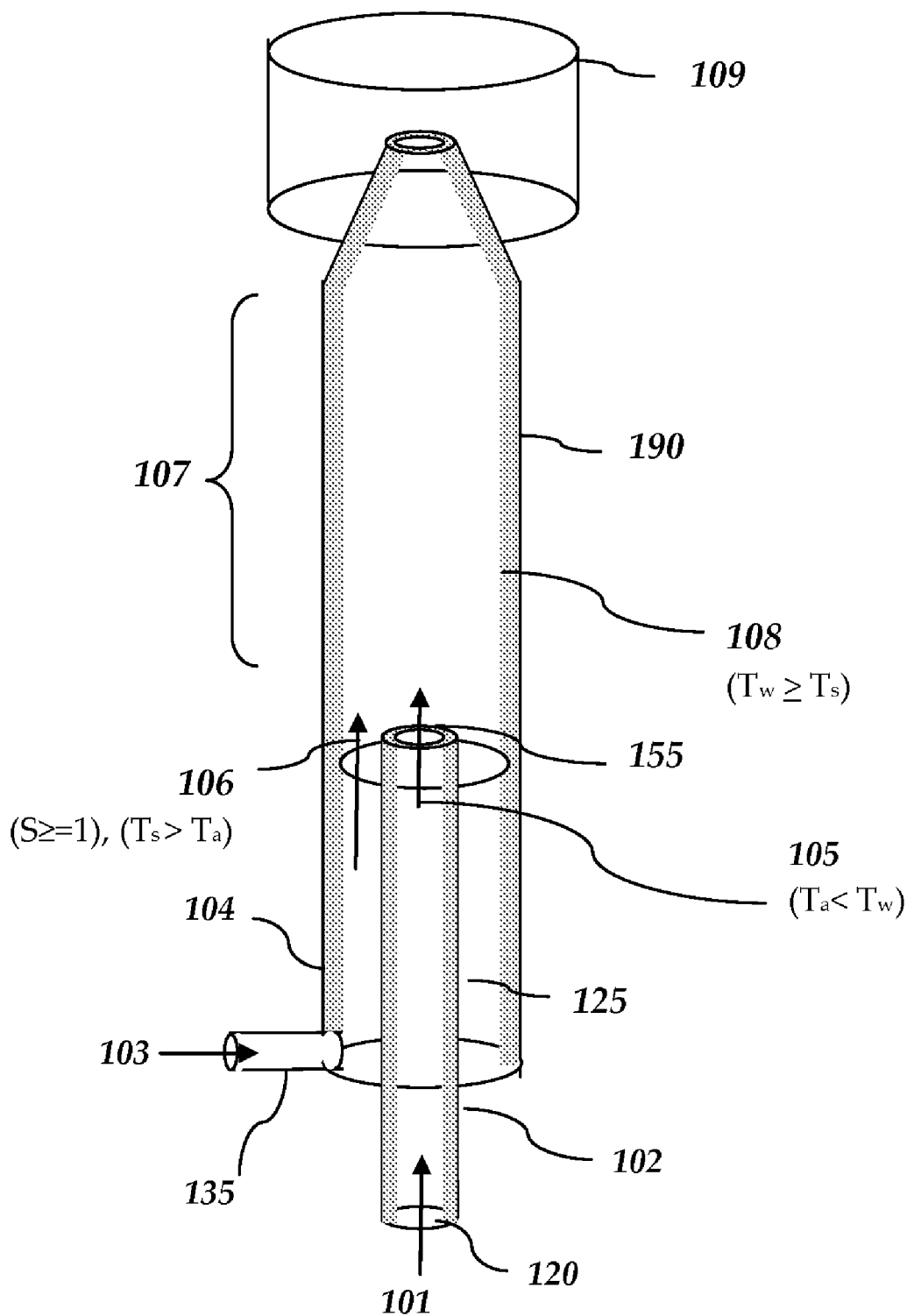
FIG. 1 depicts an embodiment of an apparatus suitable for the present invention

A first embodiment of the apparatus 190 of the technology is illustrated in FIG. 1. The apparatus 190 comprises a growth chamber 107, and aerosol conditioner 102, a sheath inlet 135 and a sheath conditioner 104 surrounding the aerosol conditioner 102, detector collector or concentrator 109 may be provided at one end of the growth chamber. An aerosol sample flow 101 is introduced at inlet 120 into an aerosol flow conditioner 102, and a sheath flow 103 is introduced at a second inlet 135 into a sheath flow conditioner 104. Generally, the aerosol sample may comprise a carrier gas and particulate. The sheath flow enters the sheath chamber 125 and is combined in a laminar manner at an outlet 155 of the aerosol conditioner in the growth chamber. The sheath flow is comprised of a condensable vapor, such as water vapor in a carrier gas. As discussed below, the sheath flow has partial pressure of condensable vapor that is at, near, or in excess of the saturation value (for example, from about 90% of saturation to well above saturation or 200% saturation). A typical carrier gas would be air. The aerosol conditioner 102 brings the existing aerosol flow 105 to a temperature (Ta). The sheath flow conditioner 104 provides the sheath flow 106 with a high water vapor content and at a temperature warmer than the temperature of the aerosol flow. The conditioned aerosol 105 and sheath 106 flows are introduced into the growth chamber 107 whose walls 108 are wet and warmer than the aerosol flow. The flows are combined in a laminar manner such that the transport of heat and vapor molecules is primarily by diffusion.

When the mass diffusivity of the condensable vapor is larger than the thermal diffusivity of the carrier gas, the diffusion of vapor into the aerosol flow is faster than the diffusion of heat. This creates a region of super-saturation, where the vapor pressure of the condensable vapor is greater than the value of the equilibrium vapor pressure at the local flow temperature. Within the region of vapor super-saturation those particles above a critical size will grow through condensation. The higher the super-saturation, the smaller the size of the particle on which the condensational growth can occur.

Once the condensational growth is initiated, the particles grow rapidly to form uniform-sized droplets. The flow containing the droplets exits from the growth chamber 107 into a particle collector or detector system 109. This detector system can be an optical device for detecting and counting the droplets, it can be an aerodynamic focusing device for concentrating the droplets, or it can be a collector for depositing the droplets onto a surface In the simplest form, sheath air is introduced at the temperature of the growth region walls with a water vapor content of approximately 100% relative humidity. Because the walls are at the same temperature and relative humidity as the sheath flow, there is no evaporative or convective cooling of the walls. This creates a sharp transition, which we have found is important to creating high values of super-saturation.

It is also possible to use a super-saturated sheath flow, where the sheath flow has a relative humidity above 100%. Such an air flow can be created using the principle of the relative rates of thermal and mass diffusivity upon which the water-condensation growth tube is based. It can also be achieved through turbulent mixing with steam or a higher temperature saturated flow. Under these conditions the maximum saturation ratio is higher than when the sheath flow is at 100% RH. With a super-saturated it is possible to create super-saturation along the centerline of the flow even if the sheath flow is near the same temperature as the aerosol flow.

As is typical of particle condensational systems, the performance is dependent on the level of super-saturation achieved within the growth region. For a fixed chemical composition, the size of the smallest particle on which condensational growth occurs depends on the extent of super-saturation. This is because the energy associated surface tension gives rise to an equilibrium vapor pressure over a droplet that is greater than over a flat surface of the same substance. The smaller the particle, the more important this effect becomes.

The level of super-saturation is characterized by the saturation ratio S, defined as the ratio of the partial pressure of the condensing vapor, $p_v$, to its equilibrium vapor pressure over a flat surface, $p_{sat,T}$, at the local flow temperature, T:

$$S=p_v/p_{sat,T},$$

Super-saturation refers to values of S is greater than 1. The relationship between S and the diameter of a particle on which condensational growth occurs can be characterized by the Kelvin relation:

$$D_{k,v}=(4\sigma_s M_w)/(p_l R_g T \cdot \ln S),$$

where $M_w$, $p_l$ and $R_s$ are the molecular weight, liquid density and surface tension of the condensing species, $R_g$ is the universal gas constant and T is the absolute temperature. $D_{k,v}$ is called the Kelvin diameter, and is a property of the condensing species equal to the diameter of a droplet of the condensing species in equilibrium with its vapor at saturation ratio S and temperature T. For the specific case of a particle that is readily wetted by, but insoluble in, the condensing vapor the Kelvin diameter is equal to the diameter of the smallest particle on which condensational growth will occur.

The saturation profiles throughout the condensing region are modeled using a two-dimensional model of convective and diffusive heat and mass transfer. For the cylindrical geometry, this is described by the two-dimensional relationships for convective and diffusive heat and mass transfer. The values of the temperature, T, throughout the condenser are obtained by solution of the partial differential equation, $$2U[1-(r/R)^2]\frac{\partial T}{\partial z}=\alpha_t\cdot\left\{\frac{1}{r}\frac{\partial}{\partial r}\left(r\frac{\partial T}{\partial r}\right)+\frac{\partial^2 T}{\partial z^2}\right\}$$

where r and z are radial and axial coordinates, respectively, R is tube radius, U is average flow velocity and $\alpha_t$ is thermal diffusivity of the flowing gas. Profiles of the partial pressure of the water vapor, $p_v$, are determined by equations analogous to (4) by replacing $\alpha_t$ with vapor diffusivity, $\alpha_v$.

$$2U[1-(r/R)^2]\frac{\partial p_v}{\partial z}=\alpha_v\left\{\cdot\frac{1}{r}\frac{\partial}{\partial r}\left(r\frac{\partial p_v}{\partial r}\right)+\frac{\partial^2 p_v}{\partial z^2}\right\}$$

In the axial direction the profiles scale as $LR_0^{-1}Pe^{-1}=\pi L\alpha_v/Q$, where L is the axial distance along the tube from the beginning of the growth region, $R_0$ is the tube radius, $\alpha_v$ is the diffusivity of water vapor, Q is the volumetric flow rate, and Pe is the mass transfer Peclet number that characterizes the relative rates of advection to diffusion. The profiles are independent of the tube radius.

For a parallel plate geometry, the temperature is described by:

$$2U[1-(x/x_o)^2]\frac{\partial T}{\partial z}=\alpha_t\left[\frac{\partial^2 T}{\partial z^2}+\frac{\partial^2 T}{\partial x^2}\right]$$

where z is in the direction of the flow, x is perpendicular distance from the centerline and $2x_O$, is the separation between the plates. The vapor distribution is described by replacing T with $p_v$ and $\alpha_t$ by $\alpha_v$. To permit calculation for non-uniform wall temperatures and for differing temperatures and vapor pressures for the entering sheath and aerosol flows, these equations were evaluated numerically under the assumption of laminar flow.

FIG. 2 shows the saturation profiles within the growth chamber calculated from these equations for the case when an aerosol flow at 20° C. and 100% RH is introduced with an equal volume of sheath air flow at 60° C. and 100% RH into a wet-walled tube at 60° C. Calculations are done for a cylindrical geometry with a combined aerosol and sheath flow of 1 L/min, and a tube diameter is $R_o$=4.6 mm. The maximum water vapor saturation achieved 1.75, which corresponds to a Kelvin diameter of 3.5 nm. These results are very similar to that indicated for an "ideal" case wherein a single flow at 20° C. is introduced into a tube with wetted walls at 60° C., without creating a finite gradient in the wall temperature. However, in practice the evaporative cooling at the walls, as well as thermal conduction to the surrounding cooler system components produces a finite gradient in the temperature at the entrance. It is the elimination of this gradient that is the primary objective of the current invention. Essentially, the sheath flow of the present technology acts as a "virtual wall", whose temperature and relative humidity are controlled by a separate "sheath flow" conditioner. With this "virtual wall" the temperature and relative humidity are effectively decoupled from the temperature of the entering aerosol flow.

Yet higher super-saturation values may be attained by increasing the temperature difference between the entering aerosol flow and the sheath flow. FIG. 3 shows the profiles for a sheath flow at 100% RH and 76° C. surrounding a saturated aerosol flow at 0° C. This provides a peak supersaturation value of approximately 6, which corresponds to a Kelvin diameter of 1.3 nm.

FIGS. 4 and 5 show water vapor super-saturation profiles achieved with a commercial device built in accordance with U.S. Pat. No. 6,712,881. For both, the temperature of the wetted walls is set equal to the temperature of the sheath. The sheath flow is introduced at the same temperature and relative humidity as the aerosol flow, with a short gradient in the temperature of the wetted wall at the entrance of the growth region. In FIG. 4 the entering flow is at 20° C. and 100% RH, with a wall temperature increasing from 20° C. at the entrance to 45° C. within 2 tube diameters, then more slowly to 55° C. by 11 tube diameters. In FIG. 5 the entering flow is at 0° C. and 100% RH, and the wall temperature increases to 65° C. within 2 tube diameters, and increases gradually to 76° C. over the remaining length.

Comparing the results of the device of FIG. 1 to those of a device formed in accordance with U.S. Pat. No. 6,712,881, wherein the sheath and aerosol flows are introduced into the growth region at the same temperature and relative humidity, illustrates advantages of the present technology. A comparison may be performed by passing all of the flow through a single, wet-walled tube, the first portion of which is held at 20° C., and the second portion is heated to 60° C. If it were possible in the device built in accordance with U.S. Pat. No. 6,712,881 to create a step-function change in the wall temperature from the "conditioned" value of 20° C. to the "growth region" temperature of 60° C., then it would be possible to achieve saturation profiles similar to those shown in FIG. 2. Calculations assuming a sharp temperature discontinuity indicate a maximum saturation value of approximately 1.8, which is sufficient to activate the growth of particles as small as 3.2 nm in diameter. However, in practice, it is not possible to achieve a sharp increase in temperature at the entrance of the growth region because of evaporative and convective cooling at the walls from the entering flow. Instead, there is a finite gradient in the temperature along the direction of the flow. The actual saturation profiles achieved in the warmed portion of the tube are like those shown in FIG. 4, wherein calculations are done assuming a gradient of in wall temperature at the growth tube entrance. The result is a decrease in the maximum saturation achieved, and a corresponding to a particle activation diameter, of 5.5 nm, in agreement with that measured. (See. T. Petäjä; G. Mordas; H. Manninen; P. P. Aalto; K. Hämeri; M. Kulmala, Detection Efficiency of a Water-Based TSI Condensation Particle Counter 3785, *Aerosol Science and Technology;* 2006; 40:1090-1097, S V. Hering; M R. Stolzenburg; Fr R. Quant; D R. Oberreit; P B. Keady. A Laminar-Flow, Water-Based Condensation Particle Counter (WCPC) *Aerosol Science and Technology;* 2005; 39: 659-672)

Figure 3:
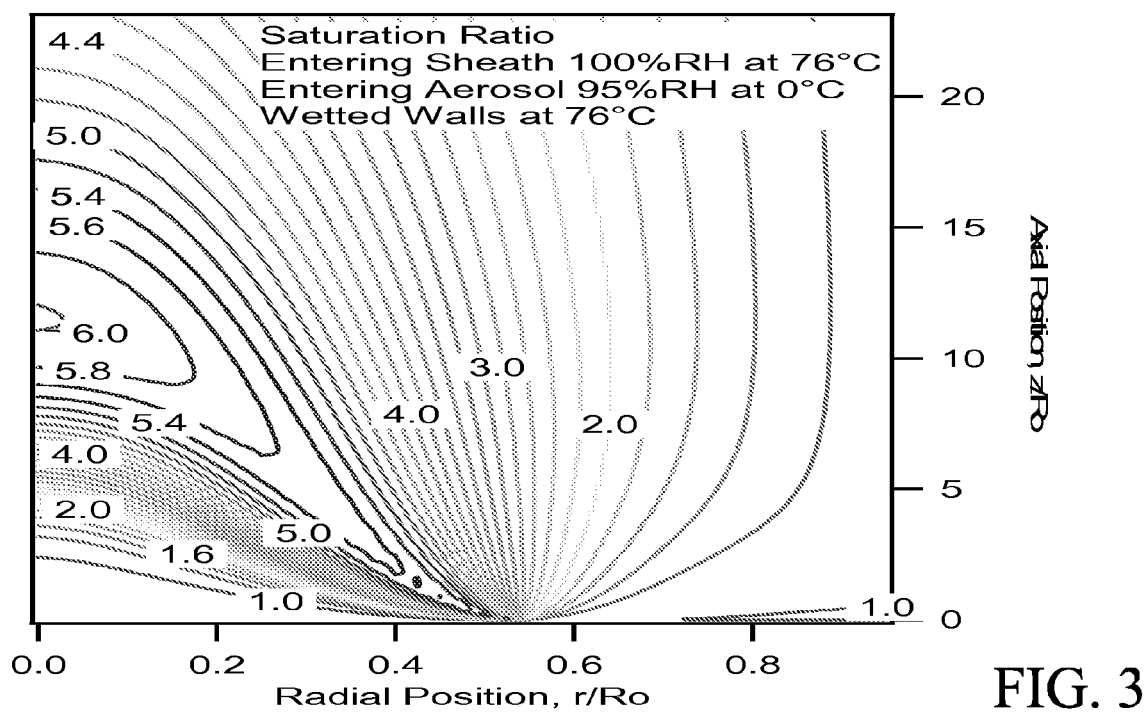
FIG. 3 illustrates saturation profiles achieved when sheath flow at, or near, 100% relative humidity and surrounds a colder, saturated air flow in a wet-walled tube where sheath is at 76° C. and the aerosol is at 0° C. and the walls of the wet-walled tube are 76° C.
Figure 5:
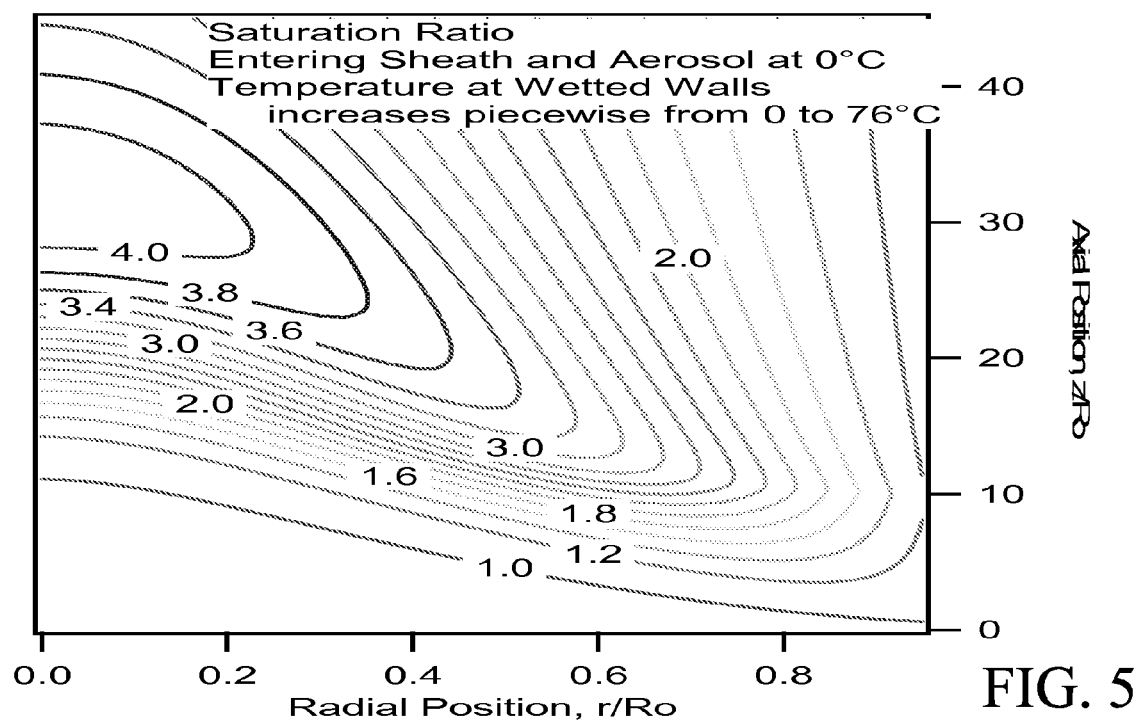

When operating at larger temperature differences, the presence of a gradient in the wall temperature has an even larger effect. The calculations of FIG. 3 show the saturation profiles in the growth region when a sheath flow at 100% RH and 76° C. surrounds an aerosol flow at 0° C. are very similar to that calculated for the "ideal" case discontinuous increase in the temperature wetted wall from 0° C. to 76° C. However, when the temperature at the entrance of the growth region is ramped from 0° C. to 65° C. over a distance of 2 tube diameters, and then subsequently increases to 76 over its remaining length, the peak saturation is reduced from 6.0 to 4.2, as shown in FIG. 5.

Another advantage of controlling the sheath flow conditions separately from that of the aerosol flow is that it becomes possible create a sheath that is already super-saturated.

Figures 6, 7:
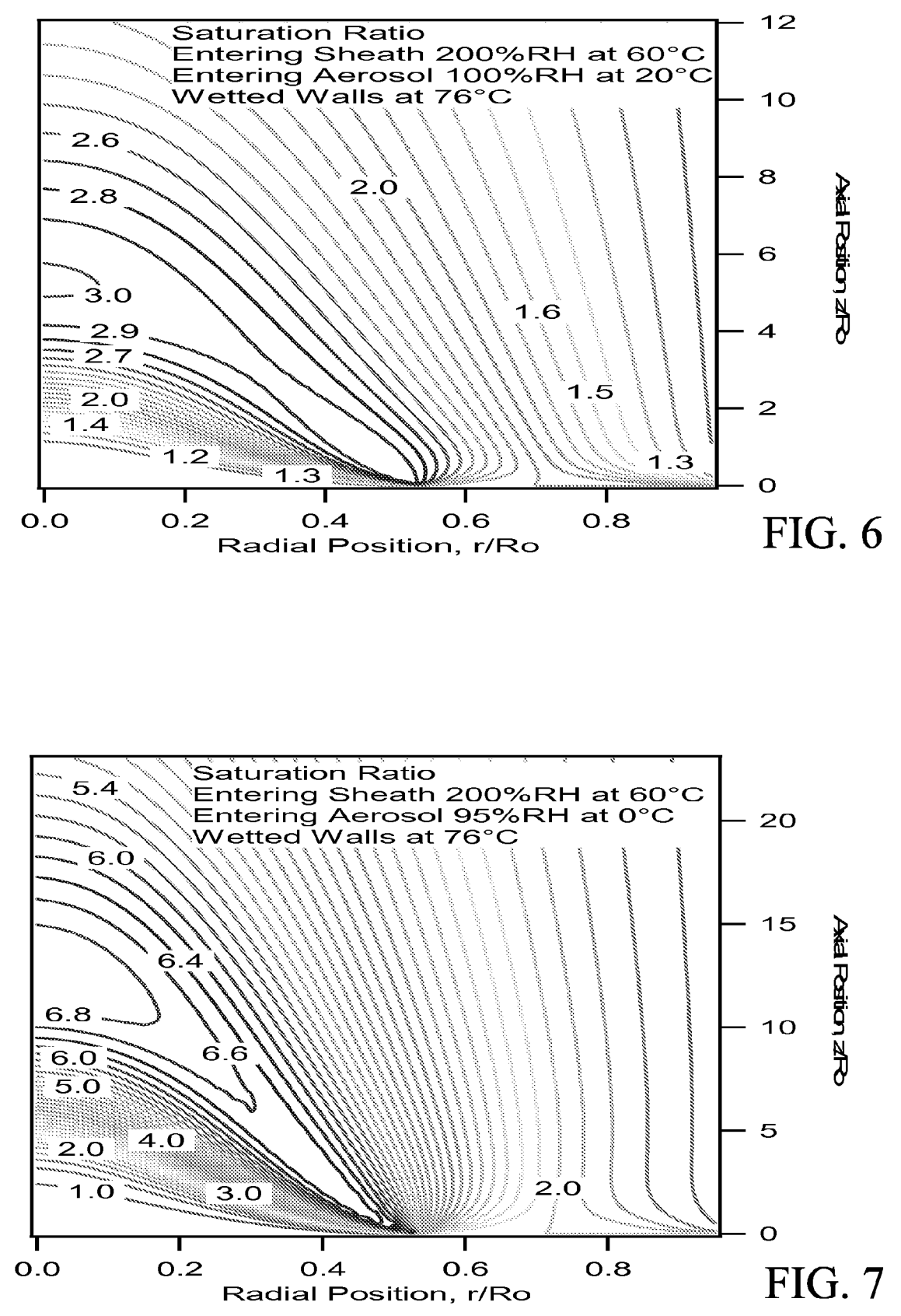

FIG. 6 shows the profile of water vapor saturation ratio that results when an aerosol flow at 20° C. is introduced along with an equal volume of sheath flow at a temperature of 60° C. and a relative humidity of 200% into a growth tube whose wetted walls are at 76° C. The system geometry is the same as in FIG. 2, with tube diameter of 4.6 mm, with equal sheath and aerosol flows of 0.5 L/min (for a total flow of 1 L/min). The temperature of growth tube to chosen to approximately match the equilibrium vapor pressure at the growth tube wall to the water vapor pressure of the sheath flow. Under these conditions the maximum saturation ratio is near 3, which is sufficient to activate particle growth for particles smaller than 2 nm in diameter. When the entering sheath flow is supersaturated it is possible to create super-saturation along the centerline of the flow even if the sheath flow is near the same temperature as the aerosol flow. FIG. 7 shows the profiles that result when the sheath flow at 200% RH and 76° C. surrounds an aerosol flow at 0° C. The peak saturation ratio reaches 6.9 as compared to 6.0 when the sheath is at 100% RH.

Figure 8:
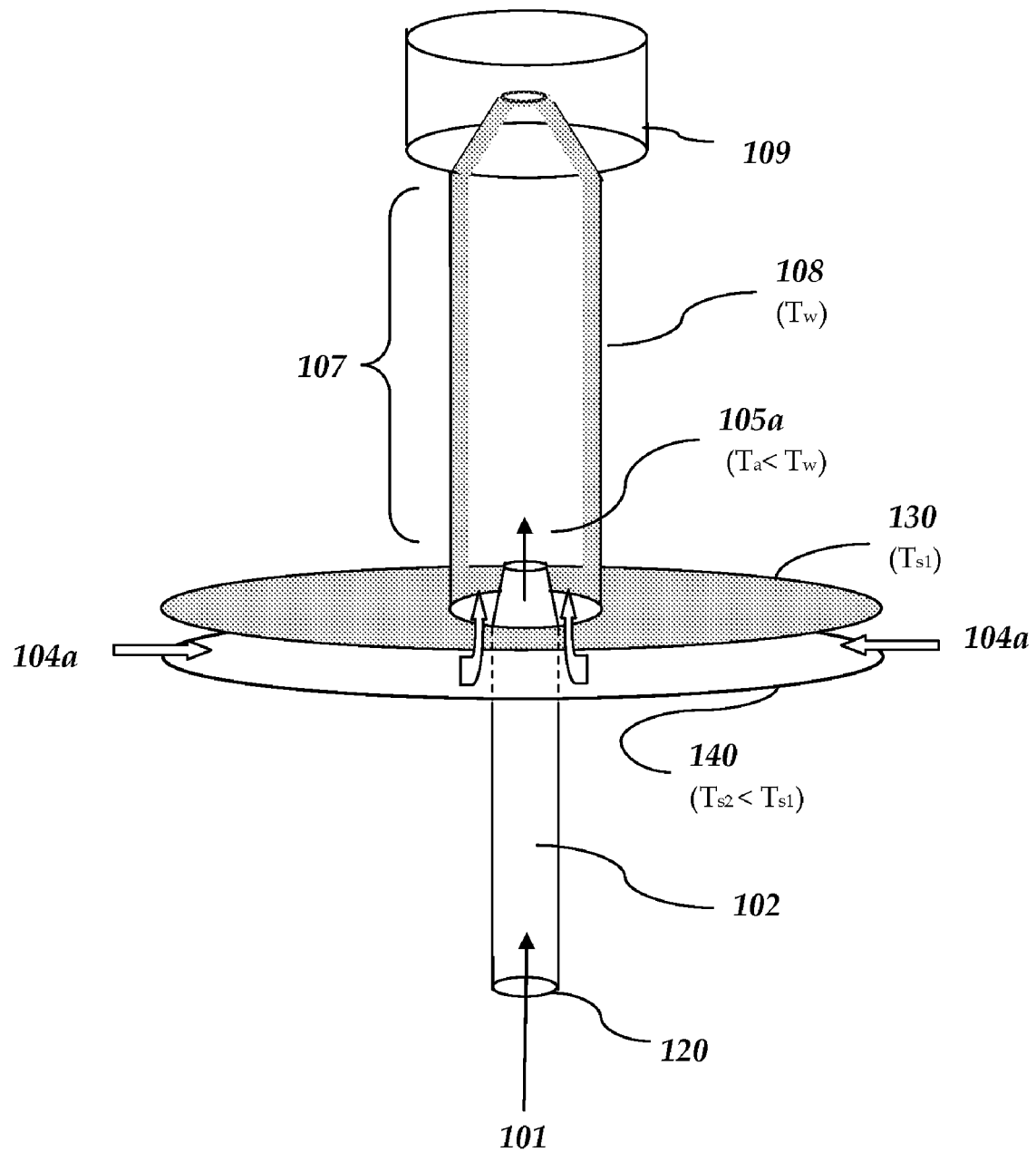
FIG. 8 depicts an embodiment of an apparatus suitable for the present technology showing a method of obtaining a supersaturated sheath flow.
Figure 9:
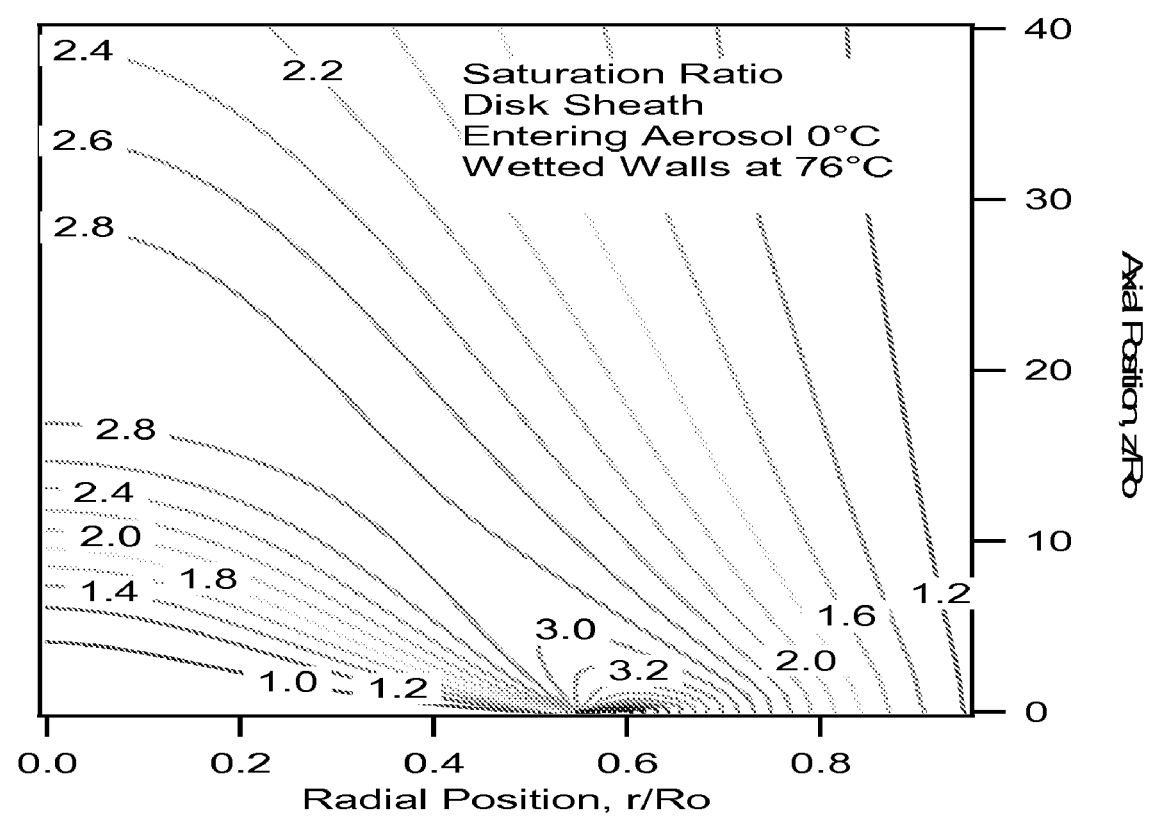

FIG. 8 shows illustrates an approach for achieving a super-saturated sheath flow using the principle of the relative rates of thermal and mass diffusivity in a laminar flow. A radially-directed, laminar sheath flow 101 is introduced between two plates, 130, 140 that comprise a sheath flow conditioner. The upper plate 130 is held at a temperature $T_{s1}$ that is warmer than the temperature of the lower plate 140, $T_{s2}$. In the simplest case, the upper plate is at the temperature of the walls of the growth region 104 ($T_{s1}=T_w$), and the lower plate is at the temperature of the walls of the aerosol preconditioner, 102 ($T_{s2}=T_a$). Additionally, the upper surface 130 is configured to provide a vapor pressure of water vapor near the surface is close to the saturation value at the surface temperature. This can be accomplished by using a porous surface that is continuously wetted. Alternatively, it may be achieved using Nafion® membrane (available from DuPont) with liquid water above. By placing making the upper plate the warmer, wet surface, the flow is stable with respect to buoyancy-driven convection, and the flow remains laminar. As in the calculations described above, the water vapor diffuses into the flow more quickly than the flow warms, creating a region of vapor super-saturation between the two plates. This flow 104a is introduced in a sheath around the aerosol flow 105a at the entrance of the growth region 107. As the flow proceeds through the growth region, the water vapor diffuses into the aerosol flow, creating a region of vapor super-saturation, particle activation and condensational growth. The saturation profiles in the growth region are shown in FIG. 9. This geometry reduces the radial dependence of the saturation ratio, with a value of 2.8 extending throughout the aerosol region.

Table 1 below summarizes the above results. Comparison is also given to the case of prior art where the temperature and relative humidity of the sheath and aerosol flows are approximately equal. In these examples, calculations have been done for tubular geometry. Extension to other geometries is possible, as the results are based on the fundamental difference in heat in air and mass transfer of water vapor. The concept described here can also be extended to a multitude of flows, similarly joined in a laminar manner.

TABLE 1

Comparison of Peak Super-Saturation and Minimum Activation Diameter for the Current Diffusive Mixing and Prior Laminar Flow Systems for

Figure 2:
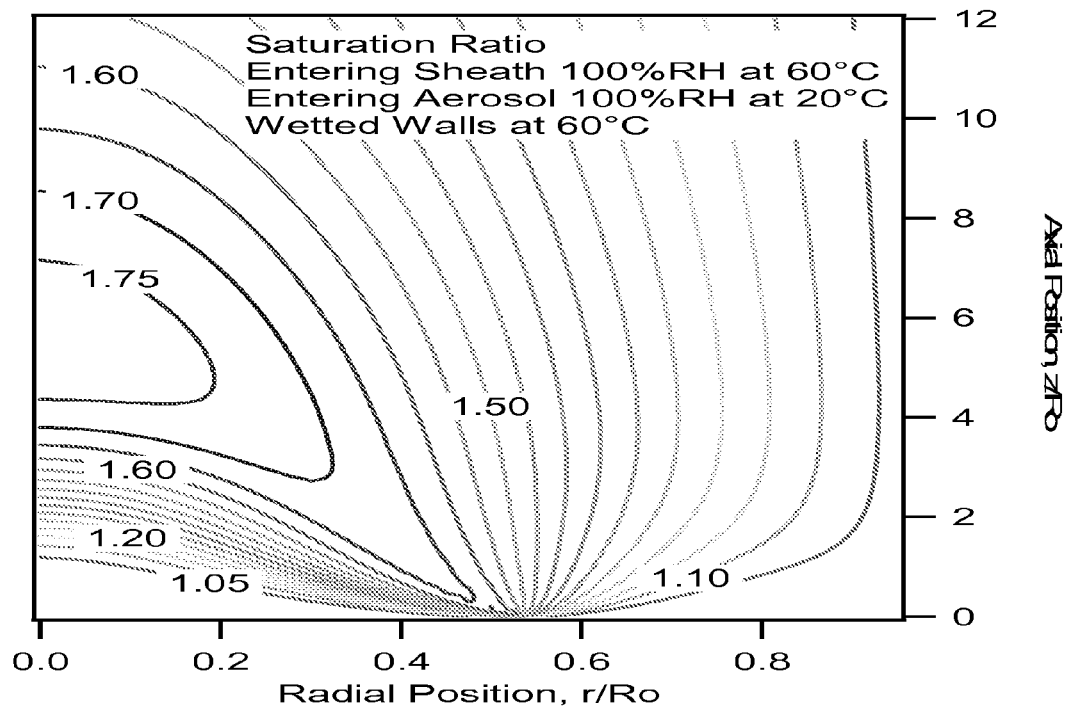
FIG. 2 illustrates saturation profiles achieved when sheath flow at, or near, 100% relative humidity and surrounds a colder, saturated air flow in a wet-walled tube wherein the sheath temperature is 60° C., the aerosol temperature is 20° C. and the walls of the wet-walled tube are 60° C.
Figure 4:
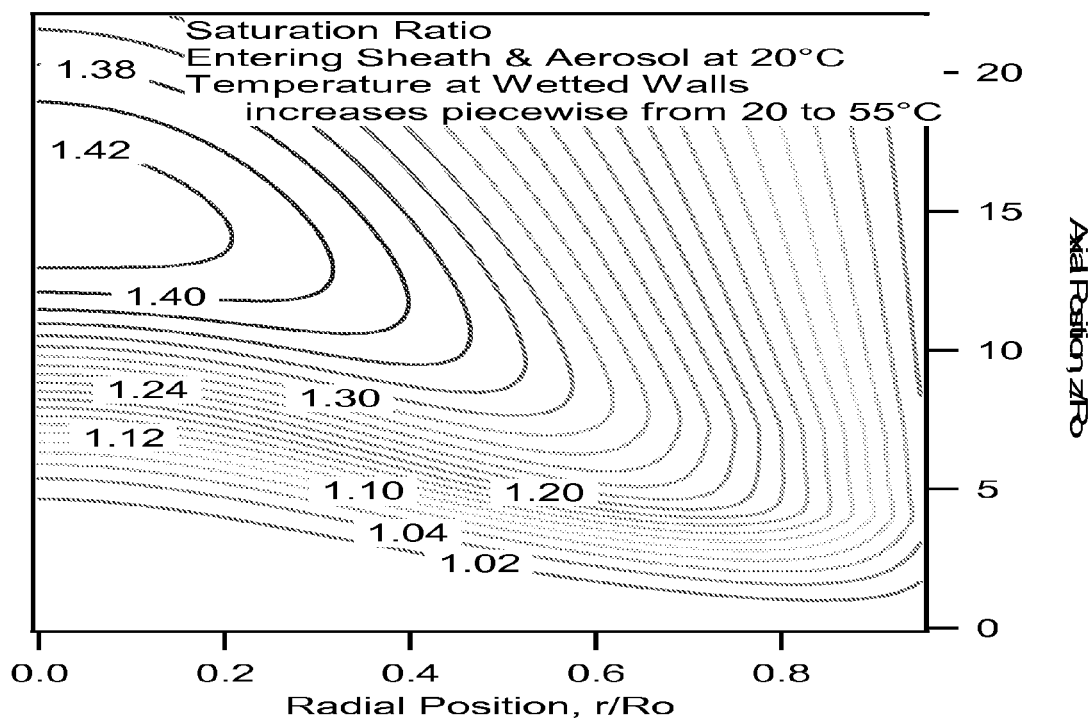
FIGS. 4 and 5 show water vapor super-saturation profiles achieved with a commercial device built in accordance with U.S. Pat. No. 6,712,881.

| Test | Entering Sheath Flow T (° C.)/RH (%) | Entering Aerosol Flow T (° C.) | Temperature of Wetted Wall T (° C.) | $S_{max}$ | $D_{act}$ (nm) | Notes |
|---|---|---|---|---|---|---|
| Diffusive Mixing Configurations (present invention) ||||||||
| A | 60/100 | 20/100 | 60 | 1.8 | 3.5 | FIG. 2 |
| B | 76/100 | 0/95 | 76 | 6.0 | 1.3 | FIG. 3 |
| A | 60/200 | 20/100 | 76 | 3.0 | 1.8 | FIG. 6 |
| B | 60/200 | 0/95 | 76 | 6.9 | 1.2 | FIG. 7 |
| C | disk sheath | 0/95 | 76 | 2.9 | 1.9 | FIG. 9 |
| Equal Temperature and RH or Sheath and Aerosol (prior art) ||||||||
| A, D | 20/100 | 20/100 | 60 | 1.4 | 5.5 | FIG. 4 |
| B, D | 0/100 | 0/100 | 76 | 4.2 | 1.6 | FIG. 5 |

Legend:
A Total flow is 1.0 L/min. Tube diameter is 9.2 cm. Aerosol and sheath flows are equal.
B Total flow is 1.2 L/min. Tube diameter is 3.8 cm. Aerosol and sheath flows are equal.
C Prior to entering tube, sheath flow passes between two wetted disks, the upper one of which is held at 76° C., and the lower one is at 0° C. Aerosol and sheath flows are equal.
D The temperature at the walls of the tube increase in a piecewise manner.

Although the subject matter has been described in language specific to structural features and/or methodological acts, it is to be understood that the subject matter defined in the appended claims is not necessarily limited to the specific features or acts described above. While the invention has been described with respect to a carrier gas of air and a condensable vapor of water, the invention is applicable to any system for which the mass diffusivity of the condensable vapor is greater than the thermal diffusivity of the carrier gas. An example of another condensable vapor system would be methanol (MW=32) vapor in a carbon dioxide (MW=44) or Argon (MW=40) carrier gas. The specific features and acts described above are disclosed as example forms of implementing the claims.

What is claimed is:

1. A method for producing particle growth via condensation of vapors, comprising:
   providing a growth chamber having wetted walls at a first temperature;
   introducing a sheath flow at a second temperature, the sheath flow comprising at introduction at least in part a condensable vapor having a partial pressure near or at a saturation value of the vapor at the first temperature;
   introducing a particle laden flow in a laminar manner with the sheath flow, the particle laden flow being introduced at a third temperature lower than the first temperature and the second temperature;
   the partial pressure of the condensable vapor in the sheath flow being selected to be higher than a saturation partial pressure of the condensable vapor at the third temperature to create diffusive mixing of the condensable vapor in the particle and sheath flows in a region separated from the walls of the growth chamber.

2. The method of claim 1 further including the step of maintaining a vapor pressure of a condensing vapor at walls of the growth chamber near saturation.

3. The method of claim 1 wherein first temperature is in a range of about 30 degrees C. to about 80 degrees C.

4. The method of claim 1 wherein the second temperature is in a range of about 30 degrees C. to about 80 degrees C.

5. The method of claim 4 wherein a relative humidity of the sheath flow is in a range of about 100% to 200%.

6. The method of claim 1 wherein the third temperature is in a range of about 0 to 30 degrees C.

7. The method of claim 6 wherein a relative humidity of the particle laden flow is in a range of about 80 to 100%.

8. The method of claim 1 wherein the sheath flow has a saturation ratio greater than one.

9. The method of claim 1 wherein the temperature of the walls of the growth chamber is selected such that an equilibrium vapor pressure of a condensing vapor at the first temperature is close to the absolute vapor pressure of a condensing vapor in the sheath flow.

10. A method for producing particle growth via condensation of vapors, comprising:

providing a growth chamber having walls at a first temperature [Tw];

introducing a sheath flow having a flow volume at a second temperature [Ts] and including a condensable vapor having a partial pressure in the sheath flow at or near its saturation value and approximately equal to equilibrium partial pressure at the first temperature;

introducing particle laden flow of equal volume into the sheath flow in a laminar manner with the sheath flow at a third temperature [Ta] lower than the first temperature and the second temperature.

11. The method of claim 10 wherein first temperature is in a range of about 40 degrees C. to about 80 degrees C.

12. The method of claim 11 wherein the second temperature is in a range of about 40 degrees C. to about 80 degrees C.

13. The method of claim 11 wherein the third temperature is in a range of about 0-20 degrees C.

14. The method of claim 1 wherein the method further includes providing a sheath flow conditioner having a first of said wetted walls at a fourth temperature; and a second of said wetted walls at a fifth temperature lower than the fourth temperature.

15. The method of claim 14 wherein the fourth temperature equals the first temperature and the fifth temperature equals the third temperature.

16. A method for producing particle growth via condensation of vapors, comprising: providing a growth chamber having walls at a first temperature; introducing a sheath flow at a second temperature and at a relative humidity of the sheath flow is in a range of greater than 100% up to 200%, the sheath flow comprising at introduction at least in part a condensable vapor having a partial pressure near a saturation value of the vapor at the first temperature; introducing a particle laden flow in a laminar manner with the sheath flow, the particle laden flow being introduced at a third temperature lower than the second temperature.

17. The method of claim 1 wherein the first and second temperatures are warmer than the third temperature by at least 10 degrees C. or greater.

* * * * *

UNITED STATES PATENT AND TRADEMARK OFFICE
CERTIFICATE OF CORRECTION

| | |
|---|---|
| PATENT NO. | : 7,736,421 B2 |
| APPLICATION NO. | : 11/868163 |
| DATED | : June 15, 2010 |
| INVENTOR(S) | : Hering et al. |

It is certified that error appears in the above-identified patent and that said Letters Patent is hereby corrected as shown below:

Col. 10, line 21: After "claim" and before "wherein", delete "11" and substitute therefore --12--

Signed and Sealed this

Seventh Day of December, 2010

David J. Kappos
*Director of the United States Patent and Trademark Office*